US012295643B2

(12) United States Patent
Hitzeroth et al.

(10) Patent No.: US 12,295,643 B2
(45) Date of Patent: May 13, 2025

(54) INTRAVASCULAR NEEDLE WITH FLEX CIRCUIT

(71) Applicant: Biosense Webster (Israel) Ltd., Yokneam (IL)

(72) Inventors: Matthew Hitzeroth, Irwindale, CA (US); Daniele Ghidoli, Irwindale, CA (US); Raymond Yue-Sing Tang, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 421 days.

(21) Appl. No.: 17/094,402

(22) Filed: Nov. 10, 2020

(65) Prior Publication Data

US 2021/0169562 A1 Jun. 10, 2021

Related U.S. Application Data

(60) Provisional application No. 62/943,552, filed on Dec. 4, 2019.

(51) Int. Cl.
*A61B 18/14* (2006.01)
*A61B 18/00* (2006.01)
(Continued)

(52) U.S. Cl.
CPC ...... *A61B 18/1477* (2013.01); *A61B 18/1206* (2013.01); *A61B 18/1492* (2013.01);
(Continued)

(58) Field of Classification Search
CPC . A61B 18/1477; A61B 18/1492; A61B 18/14; A61B 18/082; A61B 2018/00077;
(Continued)

(56) References Cited

U.S. PATENT DOCUMENTS 5,558,673 A * 9/1996 Edwards ............ A61B 18/1477
606/41
8,079,982 B1 * 12/2011 Ponzi ................. A61B 18/1492
604/95.01
(Continued)

FOREIGN PATENT DOCUMENTS

AU 2014268215 A1 6/2015
CN 105899157 B 8/2019
(Continued)

OTHER PUBLICATIONS

International Search Report & Written Opinion dated Feb. 25, 2021, from corresponding International application No. PCT/US2020/060869.
(Continued)

*Primary Examiner* — Khadijeh A Vahdat
*Assistant Examiner* — Marina Delaney Templeton

(57) ABSTRACT

Ablation and diagnostic tools having a wrapped flexible circuit are provided. The wrapped flexible circuit can include one or more electrodes on a surface layer, one or more conductive traces on one or more lower layers, and an electrically insulating substrate. The surface layer can be patterned to have multiple electrodes. The lower layer(s) can include electrode contact trace(s) and/or traces for forming thermocouple junctions. The wrapped flexible circuit can be affixed to an outer surface of a metallic tube. The electrodes can be electrically isolated from the metallic tube. The metallic tube can have a sharp end to puncture tissue during ablation or intravascular diagnostic procedure. Additionally, or alternatively, the wrapped flexible circuit can have a pointed end and sufficient structural integrity to puncture tissue during ablation or intravascular diagnostic procedure without the support of a metallic tube.

13 Claims, 8 Drawing Sheets

(51) Int. Cl.
*A61B 18/12* (2006.01)
*A61B 34/20* (2016.01)

(52) U.S. Cl.
CPC .... *A61B 34/20* (2016.02); *A61B 2018/00077* (2013.01); *A61B 2018/00083* (2013.01); *A61B 2018/00577* (2013.01); *A61B 2018/00821* (2013.01); *A61B 2034/2046* (2016.02)

(58) Field of Classification Search
CPC ........... A61B 2018/00083; A61B 2018/00821; A61B 2018/00791; A61B 2018/00797; A61B 2018/00577; A61B 2018/00642; A61B 2018/1425; A61B 2018/1427; A61B 2018/1467; A61B 2018/00345; A61B 2018/00839; A61B 17/3403; A61B 5/01; A61B 5/262; A61B 5/287; A61B 5/150412; A61B 5/150389; A61B 5/6848; A61B 5/282; A61B 5/283; A61B 2017/00247; A61B 2017/00053; A61B 2562/164; A61B 2562/166; A61B 2562/04; H05K 2201/051
See application file for complete search history.

(56) References Cited

U.S. PATENT DOCUMENTS

| | | | |
|---|---|---|---|
| 9,326,813 B2 | 5/2016 | Pike, Jr. et al. | |
| 2006/0030849 A1* | 2/2006 | Mirizzi | A61F 7/123 606/50 |
| 2007/0219551 A1* | 9/2007 | Honour | A61B 5/6852 606/41 |
| 2009/0143651 A1* | 6/2009 | Kallback | A61B 5/287 600/374 |
| 2009/0240249 A1* | 9/2009 | Chan | A61B 18/1492 606/41 |
| 2013/0090525 A1* | 4/2013 | Seymour | H05K 3/10 607/116 |
| 2016/0073960 A1 | 3/2016 | Jung et al. | |
| 2016/0228061 A1* | 8/2016 | Källbäck | A61B 5/0215 |
| 2018/0271402 A1 | 9/2018 | Osadchy et al. | |
| 2019/0175271 A1* | 6/2019 | Beale | A61N 5/045 |
| 2021/0022803 A1* | 1/2021 | Olson | A61B 18/1492 |

FOREIGN PATENT DOCUMENTS

| | | |
|---|---|---|
| JP | H10243947 A | 9/1998 |
| JP | 2001037775 A | 2/2001 |
| JP | 2002532186 A | 10/2002 |
| JP | 2013520269 A | 6/2013 |
| JP | 2016064152 A | 4/2016 |
| JP | 2016511025 A | 4/2016 |
| WO | 2006/052905 A2 | 5/2006 |
| WO | 2015/103617 A1 | 7/2015 |
| WO | 2016130713 A1 | 8/2016 |
| WO | 2017/214183 A1 | 12/2017 |
| WO | 2018/067540 A1 | 4/2018 |
| WO | 2019/046769 A1 | 3/2019 |

OTHER PUBLICATIONS

International Preliminary Report on Patentability dated May 17, 2022, from corresponding International application No. PCT/US2020/060869.
Notification of Reasons for Refusal & English-Machine translation dated Mar. 5, 2024, from corresponding Japanese Application No. 2022-533524.
Notification of Reasons for Refusal & English-Machine translation dated Sep. 3, 2024, from corresponding Japanese Application No. 2022-533524.
Written Opinion & English translation dated Nov. 28, 2024, from corresponding Japanese Application No. 2022-533524.
Decision to Grant & English-Machine translation dated Dec. 10, 2024, from corresponding Japanese Application No. 2022-533524.

* cited by examiner

INTRAVASCULAR NEEDLE WITH FLEX CIRCUIT

CROSS REFERENCE TO RELATED APPLICATIONS

This application claims the benefit of priority under the Paris Convention as well as 35 U.S.C. §§ 119 and 120 to prior filed U.S. Provisional Patent Application No. 62/943,552 filed on Dec. 4, 2019 which is hereby incorporated by reference as set forth in full herein.

FIELD

The present invention generally relates to intravascular catheter systems, and more particularly, to electrodes for intravascular ablation and/or diagnostics.

BACKGROUND

Various catheters are available that deliver electrodes to cardiac or other tissues of the body for the purpose of ablation, diagnostics, and other functions to aid in medical treatments.

Electrodes used for ablation can be configured to deliver concentrated radiofrequency (RF) current to tissue to create thermal injury of tissue in contact with the electrode. Insufficient heating can result in an insufficiently sized lesion while overheating of the electrode can cause evaporation of tissue or blood water and steam bubble formation that can uncontrollably and undesirably rupture tissue. Accurate temperature measurement during ablation can be challenging due to placement of thermocouples in relation to the electrodes. In some applications, it can be advantageous to puncture tissue so that an electrode can be placed within the tissue; however, abrupt electrode geometry shaped to puncture tissue can lead to non-uniform current distribution during ablation and therefore hot spots. To avoid inadvertently puncturing tissue by a sharp electrode, the electrode can be sheathed during intravascular delivery; however, it can be difficult to ascertain whether the electrode is properly sheathed when the electrode is in a patient. Applicant therefore recognizes a need for improved intravascular ablation tools and methods.

Electrodes used for diagnostics are typically positioned as rings spaced along an atraumatic shaft at a distal end of a catheter. The atraumatic shaft can be shaped such that the rings can contact tissue. In some applications, such diagnostic catheters can be used to effectively map intravascular systems and the heart. For treatment of arrhythmias, for instance, catheter delivered electrodes can be used to map electrical properties from within the heart to locate conduction paths of signals causing the arrhythmia. Challenges associated with diagnostic catheter electrodes include increasing electrode count and capturing sub-dermal data. Increasing electrode count means increasing number of electrodes and wiring to each electrode which can increase the bulk of a diagnostic catheter. A bulkier catheter can become less flexible and/or larger in diameter, increasing difficulty of delivery and positioning of the catheter during a procedure. Sub-dermal data can be captured by a structure similar to the ablation needle disclosed above; however, the needle structure includes only a singular electrode (the needle). Further, the needle structure is preferably sheathed during delivery to avoid inadvertent puncturing of tissue, and a sheath further increases the bulk of the diagnostic catheter. Applicant therefore recognizes a need for improved intravascular diagnostic electrode tools and methods.

SUMMARY

There is provided, in accordance with some embodiments of the present disclosure a device for lancing intravascular tissue that includes a tubular electrical circuit and a sharp end. The circuit has an outer surface disposed about a longitudinal axis to define a tubular shape extending along the longitudinal axis from a first end of the circuit to a proximal portion of the circuit. The circuit includes an electrically insulative substrate film, a patterned layer including electrically conductive traces that is disposed over the substrate film, an electrically insulative isolating film including one or more vias therethrough that is disposed over the patterned layer, and one or more electrodes disposed over the isolating film and on the outer surface of the tubular shape. The sharp end is affixed approximate the first end of the tubular shape of the circuit.

In some embodiments, the device includes a needle surrounded by the circuit and affixed to the circuit such that the sharp end of the device includes the tip of the needle. In some embodiments, each of the one or more electrodes is electrically isolated from the needle.

In some embodiments, the circuit has a pointed tip near the first end of the tubular shape such that the sharp end includes the pointed tip. Embodiments including the circuit with the pointed tip may or may not include a needle, metal sheet, or other structural support to maintain the tubular shape during usage of the device. In some embodiments, the tubular shape of the circuit has columnar rigidity sufficient to lance intravascular tissue with the pointed tip without relying on additional structural support to the tubular shaped circuit.

In some embodiments, the electrically insulative substrate film forms a lumen through the tubular shape and is positioned on an inner surface of the lumen. The lumen through the tubular shape can serve as a passageway for irrigation fluid without an additional structure between the insulative substrate and the irrigation passageway.

In some embodiments, the circuit further includes a metal sheet under the electrically insulative substrate. The metal sheet includes a pointed tip approximate the first end of the tubular circuit. The sharp end includes the pointed tip of the metal sheet. The metal sheet is disposed on an inner surface of the tubular shape. The tubular shape includes the metal sheet, and the tubular shape has columnar rigidity sufficient to lance intravascular tissue.

In some embodiments, at least one of the one or more electrodes respectively includes a gold band encircling the tubular shape.

In some embodiments, the circuit further includes solder pads each electrically connected to a respective trace of the electrically conductive traces on the patterned layer. The one or more vias are positioned such that the one or more electrodes are each electrically connected to a respective trace.

In some embodiments, the solder pads are disposed at the proximal portion of the circuit.

In some embodiments, the device further includes a sheath. The sheath surrounds the electrical circuit and the sharp end. The electrical circuit and sharp end are slidable to extend the sharp end out of the sheath.

In some embodiments, the sharp end is electrically isolated from the one or more electrodes.

In some embodiments, the device includes more than one electrode and more than one via. Each electrode is electrically connected through a respective via to a respective electrically conductive trace on the patterned layer. Each electrode is electrically isolated from every other electrode.

In some embodiments, the circuit further includes one or more thermocouple junctions.

In some embodiments, the device includes a thermocouple junction positioned at a via. The thermocouple junction includes a portion of an electrode and a portion of a trace on the patterned layer, the portion of the electrode and the portion of the trace being in electrical contact with each other. In some embodiments, the electrode of the thermocouple includes gold, and the trace of the thermocouple includes constantan.

In some embodiments, the device includes a thermocouple junction residing in the patterned layer. The thermocouple junction includes respective portions of two traces on the patterned layer such the respective portions of the two traces are in electrical contact.

In some embodiments, the device includes a thermocouple junction and a needle having an outer surface. The thermocouple junction is electrically isolated from the needle. The thermocouple junction is positioned over the outer surface of the needle.

In some embodiments, the device includes a pure gold electrode having a thickness of approximately 0.001 inches (about 25 micrometers).

In some embodiments, the device has more than one electrode and more than one thermocouple junction. Each thermocouple junction is positioned to be heated by a respective electrode. Some or all of the thermocouple junctions include a portion of the respective electrode. Additionally, or alternatively, some or all of the thermocouple junctions are each respectively positioned in the patterned layer, below the respective electrode and electrically isolated from the respective electrode.

In some embodiments, the device further includes a navigation sensor positioned to detect a movement of one or more electrodes.

In some embodiments, the navigation sensor is positioned to detect movement, in relation to the navigation sensor, of at least two electrodes of the one or more electrodes.

In some embodiments, the device further includes a catheter having a distal end, a needle assembly including the circuit and the sharp end, and a navigation sensor. The needle assembly is translatable in one dimension in relation to the navigation sensor. The navigation sensor is affixed near the distal end of the catheter. The navigation sensor is positioned to detect movement, in relation to the navigation sensor, of one or more electrodes.

In some embodiments, the device includes more than one electrode, more than one via, and more than one electrically conductive trace. The circuit further includes solder pads. Each of the electrodes are electrically connected through a respective via to a respective trace. The solder pads are each electrically connected to a respective electrically conductive trace.

In some embodiments, at least one of the electrodes is electrically isolated from every other electrode.

In some embodiments, one or more electrodes are configured to measure a voltage and/or impedance.

In some embodiments, the electrodes include ring electrodes, each ring electrode circumscribing the tubular shape of the circuit.

In some embodiments, ring electrodes are spaced a predetermined distance from the sharp end. Each ring electrode is isolated, at the outer surface of the tubular shape defined by the circuit, from every other ring electrode.

In some embodiments, ring electrodes are confined to a distance of approximately 9 mm as measured from a tip of the sharp end.

In some embodiments, the circuit includes about 6 ring electrodes to about 10 ring electrodes.

In some embodiments, ring electrodes are spaced, with an edge-to-edge spacing to each neighboring ring electrode with a spacing of about 2 mm to about 4 mm.

There is further provided, in accordance with some embodiments of the present disclosure, a system including a circuit, a sharp end, a navigation sensor, and a processing device. The circuit defines an outer surface disposed about a longitudinal axis to define a tubular shape extending along the longitudinal axis from a first end of the circuit to a proximal portion of the circuit. The sharp end is affixed near the first end of the tubular shape. The circuit includes an electrically insulative substrate film, a patterned layer disposed over the substrate film, an electrically insulative isolating film disposed over the patterned layer, and a plurality electrodes disposed over the isolating film and on the outer surface of the tubular shape. The patterned layer includes electrically conductive traces. The electrically insulative isolating film includes one or more vias therethrough. The navigation sensor is positioned to detect movement, in relation to the navigation sensor, of an electrode of the one or more electrodes. The processing device is configured to extract electrical measurements from the plurality of electrodes and determine, using the navigation sensor, a position of each of the plurality of electrodes in relation to intracardial tissue.

In some embodiments, the one or more electrodes include a plurality of ring electrodes. The processing device is further configured to determine impedance of the intracardial tissue at multiple depths of the tissue in response to lancing the intracardial tissue with the sharp end of the device and inserting the plurality of ring electrodes into the intracardial tissue.

In some embodiments, the system includes a catheter, conductive wires, and a radio frequency generator. The conductive wires are each respectively electrically connected to a respective electrically conductive trace. The conductive wires extend through the catheter. The radio frequency generator is electrically connected to at least one of the conductive wires.

There is further provided, in accordance with some embodiments of the present disclosure, a system including a circuit, a sharp end, a catheter, conductive wires, and a radio frequency generator. The circuit defines a tubular shape having an outer surface disposed about a longitudinal axis. The tubular shape extends along the longitudinal axis from a first end of the circuit to a proximal portion of the circuit. The sharp end is affixed near the first end of the tubular shape defined by the circuit. The circuit includes an electrically insulative substrate film, a patterned layer disposed over the substrate film, an electrically insulative isolating film disposed over the patterned layer, and a plurality electrodes disposed over the isolating film and on the outer surface of the tubular shape. The patterned layer includes electrically conductive traces. The insulative isolating film disposed over the patterned layer includes one or more vias therethrough. The conductive wires are each respectively electrically connected to a respective electrically conductive trace. The conductive wires extend through the catheter. The radio frequency generator is electrically connected to at least one of the conductive wires.

In some embodiments, each respective electrically conductive trace is further electrically connected to a respective electrode. The radio frequency generator, and potentially multiple radio frequency generators, are electrically connected to one or more of the conductive wires. The one or more radio frequency generators are thereby each electrically connected to a respective electrode by way of the connection of the RF generator(s) to the conductive wire(s) and the connection of the conductive wire(s) to one or more electrodes.

In some embodiments, the system includes an electrical measurement tool electrically connected to a first portion of the plurality of electrodes while the one or more radio frequency generators is electrically connected to a second portion of the plurality of electrodes. The electrical measurement tool includes a voltmeter, an ohmmeter, and/or an ammeter.

There is further provided, in accordance with some embodiments of the present disclosure, an ablation tool having a sharp end and an ablation electrode electrically isolated from the sharp end.

There is further provided, in accordance with some embodiments of the present disclosure, an ablation tool having an ablation electrode and a thermocouple that includes a portion of the ablation electrode.

There is further provided, in accordance with some embodiments of the present disclosure, a system including a catheter, a navigation sensor, and a needle assembly. The navigation sensor is positioned near the distal end of the catheter. The needle assembly includes an electrode thereon and a sharp end. The needle assembly is translatable in one dimension in relation to the navigation sensor. The needle assembly is translatable to move the sharp end out of the catheter through the distal end of the catheter. The navigation sensor is positioned to detect movement of the electrode in relation to the navigation sensor.

There is further provided, in accordance with some embodiments of the present disclosure, a method of intravascular treatment, the method including one or more of the following steps: delivering an electrode needle assembly intravascularly via a catheter, lancing tissue in or around the heart with the electrode needle assembly, and moving a first electrode of the electrode needle assembly to a first depth within the tissue while moving a second electrode of the electrode needle assembly to a position above the tissue or at a second depth shallower than the first depth.

In some embodiments, the method further includes detecting, by the first electrode, a first electrical signal at the first depth in the tissue. The first electrical signal is indicative of at least one of a tissue voltage and a tissue impendence.

In some embodiments, the method further includes applying a radio frequency electrical signal to at least one of the first electrode and the second electrode.

In some embodiments, the method further includes infusing into the tissue an electrically-conductive fluid via a lumen in the electrode needle assembly while the first electrode is positioned at the first depth.

In some embodiments, the method further includes positioning the electrode needle assembly, while sheathed, in or around the heart, positioning a navigation sensor in or around the heart, unsheathing the electrode needle assembly, while positioned in or around the heart, and detecting, by the navigation sensor, movement of at least one of the first electrode and the second electrode as a result of the unsheathing of the electrode needle assembly.

In some embodiments, the method further includes sensing a temperature approximate at least one of the first electrode and the second electrode.

There is further provided, in accordance with some embodiments of the present disclosure, a method for ablating tissue in or around the heart, the method including one or more of the following steps: delivering an electrode needle assembly intravascularly via a catheter, lancing tissue in or around the heart with a sharp end of the electrode needle assembly, moving, into the tissue, an electrode electrically isolated from the sharp end, and ablating the tissue by applying electrical energy to the electrode.

In some embodiments, the step of ablating the tissue by applying electrical energy to the electrode further includes delivering electrical current from an annular surface of the electrode to the tissue such that the electrical current comprises a substantially uniform current density across the annular surface.

There is further provided, in accordance with some embodiments of the present disclosure, a method for constructing a device for lancing intravascular tissue, the method including one or more of the following steps: applying electrically conductive traces to a first electrically insulative flexible film, positioning openings in a second electrically insulative flexible film, affixing the second electrically insulative flexible film to the electrically conductive traces and the first electrically insulative flexible film such that the openings are positioned over the electrically conductive traces, applying electrodes to the second electrical insulative flexible film such that the electrodes make contact to the electrically conductive traces through the openings in the second electrically insulative flexible film, wrapping the first electrically insulative flexible film, the electrically conductive traces, the second electrically insulative flexible film, and the electrodes to define a tubular shape extending along a longitudinal axis, and affix a sharp end near a first end of the tubular shape.

In some embodiments, the method can further include affixing an inner surface of the tubular shape to a needle such that the needle includes the sharp end affixed near the first end of the tubular shape.

In some embodiments, the method can further include electrically isolating each of the one or more electrodes from the needle.

In some embodiments, the method can further include positioning a thermocouple junction over an outer surface of the needle and electrically isolating the thermocouple junction from the needle.

In some embodiments, the method can further include forming a pointed tip at the first end of the tubular shape such that the sharp end includes the pointed tip.

In some embodiments, the method can further include forming a pointed tip at the first end of the tubular shape such that the sharp end comprises the pointed tip and forming the tubular shape to comprise columnar rigidity sufficient to lance intravascular tissue.

In some embodiments, the method can further include affixing a metal sheet under the first electrically insulative flexible film, wrapping the metal sheet to define an inner surface of the tubular shape, and forming a pointed tip on the metal sheet approximate the first end of the tubular shape such that the sharp end comprises the pointed tip.

In some embodiments, the method can further include applying a liner electrode comprising gold to the second insulative flexible film and wrapping the linear electrode to form a band encircling the tubular shape.

In some embodiments, the method can further include connecting solder pads, electrically, each to a respective electrically conductive trace of the electrically conductive traces and positioning the openings in the second electrically insulative flexible film such that the electrodes are each electrically connected to a respective trace of the electrically conductive traces.

In some embodiments, the method can further include surrounding the tubular shape and the sharp end with a sheath such that the tubular shape and sharp end are slidable to extend the sharp end out of the sheath.

In some embodiments, the method can further include electrically isolating the sharp end from the electrodes.

In some embodiments, the method can further include electrically isolating each electrode from the remainder of the electrodes.

In some embodiments, the method can further include positioning a thermocouple junction at an opening in the second electrically insulative flexible film such that the thermocouple junction comprises a portion of one of the electrodes in contact with one of the electrically conductive traces at the opening.

In some embodiments, the method can further include forming the electrode of the thermocouple junction to comprise gold and forming the electrically conductive trace of the thermocouple junction to comprise constantan.

In some embodiments, the method can further include positioning a second thermocouple junction between the first electrically insulative flexible film and the second electrically insulative film such that the second thermocouple junction comprises overlapping portions of two electrically conductive traces of the electrically conductive traces.

In some embodiments, the method can further include applying a pure gold electrode having a thickness of approximately 0.001 inches (about 25 micrometers) to the second electrically insulative film.

In some embodiments, the method can further include positioning thermocouple junctions to be heated by all of the electrodes.

In some embodiments, the method can further include positioning a navigation sensor to detect a movement of one or more of the electrodes.

In some embodiments, the method can further include positioning a navigation sensor to detect movement of two or more of the electrodes.

In some embodiments, the method can further include affixing the navigation sensor approximal a distal end of a catheter and positioning a needle assembly comprising the tubular shape and the sharp end through the catheter such that the needle assembly is confined to move in only one dimension in relation to the navigation sensor.

In some embodiments, the method can further include electrically isolating each of the electrodes from the remainder of the electrodes.

In some embodiments, the method can further include configuring the electrodes to measure a voltage and/or impedance.

In some embodiments, the method can further include wrapping the electrodes to circumscribe the tubular shape.

In some embodiments, the method can further include spacing each of the electrodes a predetermined distance from the sharp end and electrically isolating each electrode from the remainder of the electrodes.

In some embodiments, the method can further include positioning the electrodes being confined to a distance of approximately 9 mm as measured from a tip of the sharp end.

In some embodiments, the step of applying electrodes to the second electrical insulative flexible film can further include applying about 6 to about 10 linear electrodes. The method can further include wrapping each of the linear electrodes to form about 6 to about 10 ring electrodes.

In some embodiments, the method can further include spacing each of the ring electrodes with an edge-to-edge spacing to each neighboring ring electrode with a spacing of about 2 mm to about 4 mm.

There is further provided, in accordance with some embodiments of the present disclosure, a method for configuring a system for intravascular treatment, the method can include one or more of the following steps: selecting a flexible circuit, wrapping the flexible circuit to form a tubular shape, positioning a navigation sensor, and configuring a processing device. The flexible circuit is selected to have an electrically insulative substrate film, electrically conductive traces disposed over the substrate film, an electrically insulative isolating film disposed over the electrically conductive traces, the electrically insulative film comprising vias therethrough, and electrodes disposed over the isolating film and connected to at least a portion of the conductive traces through the vias. The flexible circuit is wrapped such that the electrodes are shaped as ring electrodes circumnavigating an outer surface of the tubular shape. The sharp end is affixed near a first end of the tubular shape. The navigation sensor is positioned to detect movement, in relation to the navigation sensor, of one or more of the ring electrodes. The processing device is configured to extract electrical measurements from the electrodes and determine, using the navigation sensor, a position of each of the electrodes in relation to intracardial tissue.

In some embodiments, the method further includes further configuring the processing device to determine impedance of the intracardial tissue at multiple depths of the tissue in response to lancing the intracardial tissue with the sharp end and inserting the ring electrodes into the intracardial tissue.

In some embodiments, the method further includes selecting a catheter, electrically connecting conductive wires each to a respective electrically conductive trace of the electrically conductive traces, extending the conductive wires through the catheter, and electrically connecting a radio frequency generator to at least one of the conductive wires.

In some embodiments, the method further includes connecting an electrical measurement tool electrically to a first portion of the electrodes and connecting the radio frequency generator electrically to a second portion of the plurality of electrodes.

In some embodiments the electrical measurement tool includes one or more of a voltmeter, an ohmmeter, and an ammeter.

There is further provided, in accordance with some embodiments of the present disclosure, a method for configuring a system for intravascular treatment, the method can include one or more of the following steps: selecting a flexible circuit, wrapping the flexible circuit to form a tubular shape, affixing a sharp end near a first end of the tubular shape, selecting a catheter, electrically connecting conductive wires each to a respective electrically conductive trace on the flexible circuit, and electrically connecting a radio frequency generator to at least one of the conductive wires. The flexible circuit is selected to have an electrically insulative substrate film, electrically conductive traces disposed over the substrate film, an electrically insulative isolating film disposed over the electrically conductive traces, the electrically insulative film comprising vias therethrough, and electrodes disposed over the isolating film and connected to at least a portion of the conductive traces through the vias.

There is further provided, in accordance with some embodiments of the present disclosure, a method of constructing an ablation tool, the method can include one or more of the following steps: forming an ablation electrode, forming a sharp end affixed to the ablation electrode, and electrically isolating the ablation electrode from the sharp end.

There is further provided, in accordance with some embodiments of the present disclosure, a method of constructing an ablation tool, the method can include one or more of the following steps: forming an ablation electrode and forming a thermocouple junction such that the thermocouple junction comprises a portion of the ablation electrode.

There is further provided, in accordance with some embodiments of the present disclosure, a method of constructing an ablation tool, the method can include one or more of the following steps: selecting a catheter, affixing a navigation sensor near a distal end of the catheter, positioning a needle assembly having an electrode thereon and a sharp end within the catheter such that the needle assembly is translatable in one dimension in relation to the navigation sensor, the needle assembly is translatable to move the sharp end out of the catheter through the distal end of the catheter, and configuring the navigation sensor to detect movement of the electrode in relation to the navigation sensor.

The present disclosure will be more fully understood from the following detailed description of embodiments thereof, taken together with the drawings.

DETAILED DESCRIPTION

Figure 1:
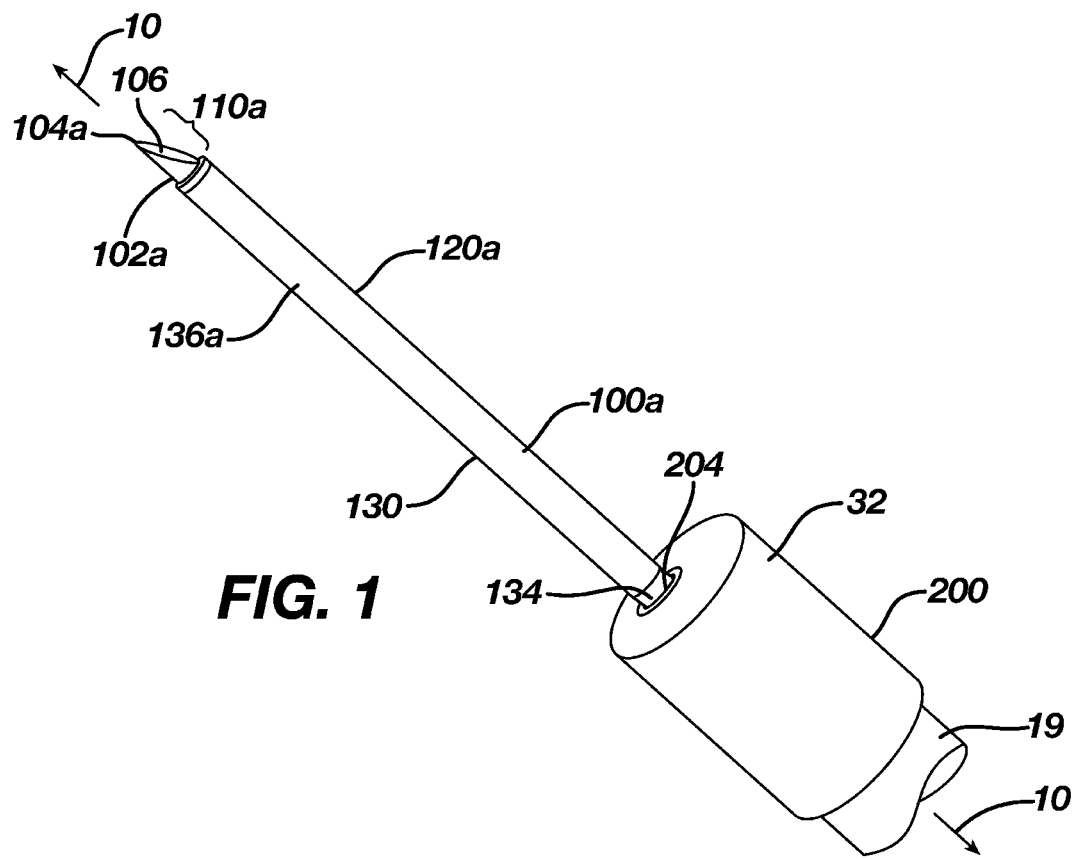
FIG. 1 is an illustration of an ablation tool in accordance with some embodiments of the present disclosure.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

As used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present disclosure.

The term "computing system" is intended to include standalone machines or devices and/or a combination of machines, components, modules, systems, servers, processors, memory, detectors, user interfaces, computing device interfaces, network interfaces, hardware elements, software elements, firmware elements, and other computer-related units. By way of example, but not limitation, a computing system can include one or more of a general-purpose computer, a special-purpose computer, a processor, a portable electronic device, a portable electronic medical instrument, a stationary or semi-stationary electronic medical instrument, or other electronic data processing apparatus.

The terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal. Computer readable medium can be non-transitory. Non-transitory computer-readable media include, but are not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable instructions and/or data.

FIG. 1 is an illustration of an ablation tool including needle assembly 100a retractable into a catheter 200 or otherwise sheathed. The needle assembly 100a can include a sharp end 110a and a flexible circuit 120a. The needle assembly 100a can include a hollow needle 102a having a pointed tip 104a and a hollow lumen 106. During an ablation treatment, conductive fluid can be delivered through the lumen 106. Lesion size can be increased by increasing thermal conductivity of tissue by delivering fluid through the needle assembly 100a in a manner similar to as disclosed in U.S. Pat. No. 9,326,813 which is hereby incorporated by reference in its entirety into this application as if set forth in full and attached in the appendix to priority application U.S. 62/943,552. During treatment, the distal, pointed end 104a of the hollow needle 102a can be introduced into tissue, electrically-conductive fluid can be infused through the needle and into the tissue, and the tissue can be ablated after and/or during introduction of the fluid into the tissue. The fluid conducts ablation energy within the tissue to create a larger lesion than would be created without introduction of the fluid. During ablation, electrical current can be supplied to the tissue via one or more electrodes 136a on the flexible circuit 120a. The flexible circuit 120a can include an electrically insulative flexible substrate. The flexible circuit 120a can be wrapped around the needle 102a to define a tubular shape. Once affixed to the needle 102a, the flexible circuit 120a is no longer flexible, meaning the circuit 120a is fixed in relation to the needle 102a. The electrode(s) 136a can be electrically isolated from the needle 102a at least by virtue of the insulative properties of the flexible substrate in addition to any intermediate insulative layers of the flexible circuit 120a.

Figure 17:
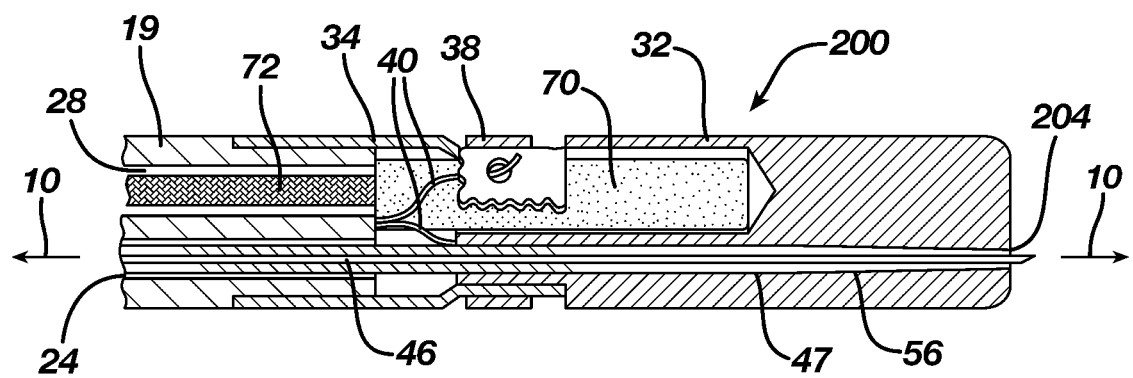
FIG. 17 is an illustration of an ablation or diagnostic tool in accordance with some embodiments of the present disclosure.

The needle assembly 100a can be slidably translatable in relation to the catheter or sheath 200 (referred to herein for simplicity as "catheter"). The catheter 200 is further illustrated in FIG. 17. Referring collectively to FIGS. 1 and 17, the needle assembly 100a can be slidably retracted into the opening 204 of the catheter 200 when the needle assembly 100a is manipulated before and after treatment. The needle assembly 100a can be sheathed to reduce the risk of inadvertently puncturing tissue. A navigation sensor 70 can be positioned in the catheter 200 near the distal end of the catheter 200. The navigation sensor 70 can be positioned and otherwise configured to detect movement of the needle assembly 100a in relation to the catheter 200. The navigation sensor can be configured to detect whether the needle assembly 100a is fully sheathed within the catheter 200. The sensor 70 can be in a fixed location in the catheter tip. In some applications the sensor 70 can be configured to provide signals to an electrode mapping system, and the electrode mapping system can determine a relative location of the needle assembly 100a based on the signals from the sensor 70. The electrode mapping system can thereby provide data indicating the status of the needle assembly 100a as being sheath/un-sheathed as well as data indicative of an intradermal signal location. Configured as such, the electrode mapping system can provide a z component of the position of the needle assembly 100a in addition to an x and y position.

Figure 2A:
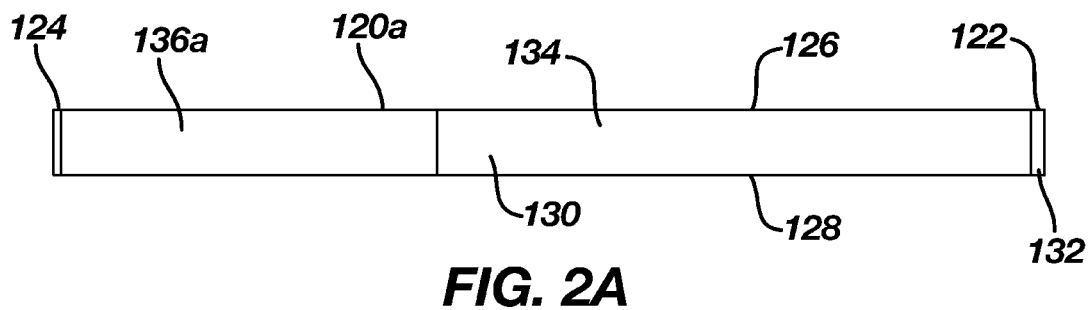
FIG. 2A is an illustration of a flexible circuit of the ablation tool of FIG. 1 in a flat configuration in accordance with some embodiments of the present disclosure.
Figure 2B:
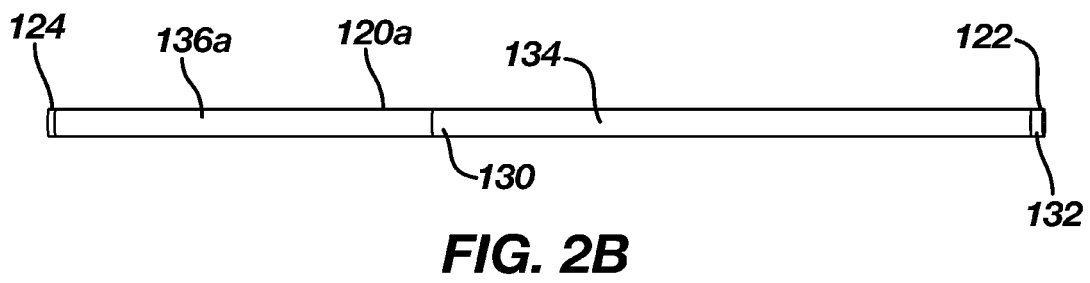
FIG. 2B is an illustration of the flexible circuit of the ablation tool of FIG. 1 in a tubular shape in accordance with some embodiments of the present disclosure.

FIG. 2A is an illustration of the flexible circuit 120a of the ablation tool of FIG. 1 in a flat configuration. FIG. 2B is an illustration of the flexible circuit 120a of the ablation tool of FIG. 1 in a tubular shape.

Referring collectively to FIGS. 1, 2A, and 2B, the flexible circuit 120a can include a rectangular flex circuit with a surface 130 at least partially covered by a sputtered gold electrode surface 136a. The rectangular flex circuit 120a can be attached by wrapping around the hollow needle 102a using adhesive and/or thermal processing. The flex circuit 120a can be electrically isolated from the needle 102a. The flex circuit 120a can further be electrically isolated from all other conductive surfaces of the ablation tool. The needle assembly 100a can include isolated trace(s) leading from the ablation electrode zone 136a to a solder pad 122 near the proximal edge 132 of the flex circuit 120a. One or more lead wires can be attached for connection back through the catheter 200 such that the lead wires ultimately connect to an RF generator. The needle 102a can be electrically isolated from the RF circuit. When the needle 102a is electrically isolated from ablation energy from the RF generator, the tip 104a of the needle 102a can have a sharp point (see also FIG. 14). When the needle 102a is not electrically isolated from ablation energy from the RF generator, the tip 104a of the needle 102a can have a rounded edge so as to mitigate non-uniform current distribution and heating during ablation (see also FIG. 15). A sharper needle generally requires less force to puncture the heart tissue. Advantages of isolating the needle tip 104a from the electrode 136a can therefore include the ability to have a sharper needle tip 104a to more easily puncture tissue and an electrode geometry shaped to further mitigate effects of non-uniform current distribution and heating during ablation.

During ablation, RF energy can be delivered from a generator to the solder pad 132, from the solder pad 132 to the flex circuit electrode 136a, from the flex circuit electrode 136a to tissue adjacent the electrode 136a, and back through system return electrode (not shown). The system return electrode can be configured in a similar manner as predicate devices. In some applications, RF energy can be delivered from the ablation zone 136a such that leakage to adjacent catheter structures such as dome and needle is minimized. The tool need not include irregular structures on the electrode surface 136a, therefore current density across ablation surface 136a can be substantially uniform.

Referring to FIG. 2A, the flexible circuit can be manufactured to a rectangular shape. The flexible circuit 120a can have a substantially uniform thickness across the area of the electrode 136a. The rectangular shape can be wrapped to define a tubular shape as illustrated in FIG. 2B and FIG. 1. In the tubular shape, the flexible circuit 120a can maintain a substantially uniform thickness in the area of the electrode 136a. The rectangular shape can be wrapped such that longitudinal sides 126, 128 of the circuit abut to create a smooth transition between the edges 126, 128 in the electrode region 136a when in the tubular shape. Configured as such, the electrode 136a can be substantially radially symmetrical about a longitudinal axis 10. Radial electrode symmetry can provide a more predictable and repeatable lesion compared to needle assemblies using the needle as an electrode. Radial electrode symmetry can provide a lesion that is less affected by the orientation of the needle assembly 100a with respect to the target tissue surface (e.g. an angled lance vs. a perpendicular lance) compared to needle assemblies using the needle as an electrode.

Risk of current leakage from the electrode 136a, through tissue or fluid, to the sharp end 110a or another needle surface can be mitigated by physically offsetting the ablation zone 136a from the sharp end 110a and the needle surface. The ablation zone 136a can be physically offset by positioning a distal edge of the ablation zone a predetermined distance from the distal end 124 of the flexible circuit 120a. The needle assembly 100a can thereby be configured to deliver essentially all of the ablation energy to targeted tissue.

Referring collectively to FIGS. 1, 2A, and 2B, the flexible circuit 120a can have an outer surface 130 that includes the electrode surface 136a and an insulated surface 134 positioned in a proximal direction in relation to the electrode surface 136a. The insulated surface 134 can electrically isolate the needle assembly 100a from the catheter 200 during ablation. The insulated surface 130 can further cover one or more electrical traces connecting the electrode 136a to the solder pad 132.

Figure 3:
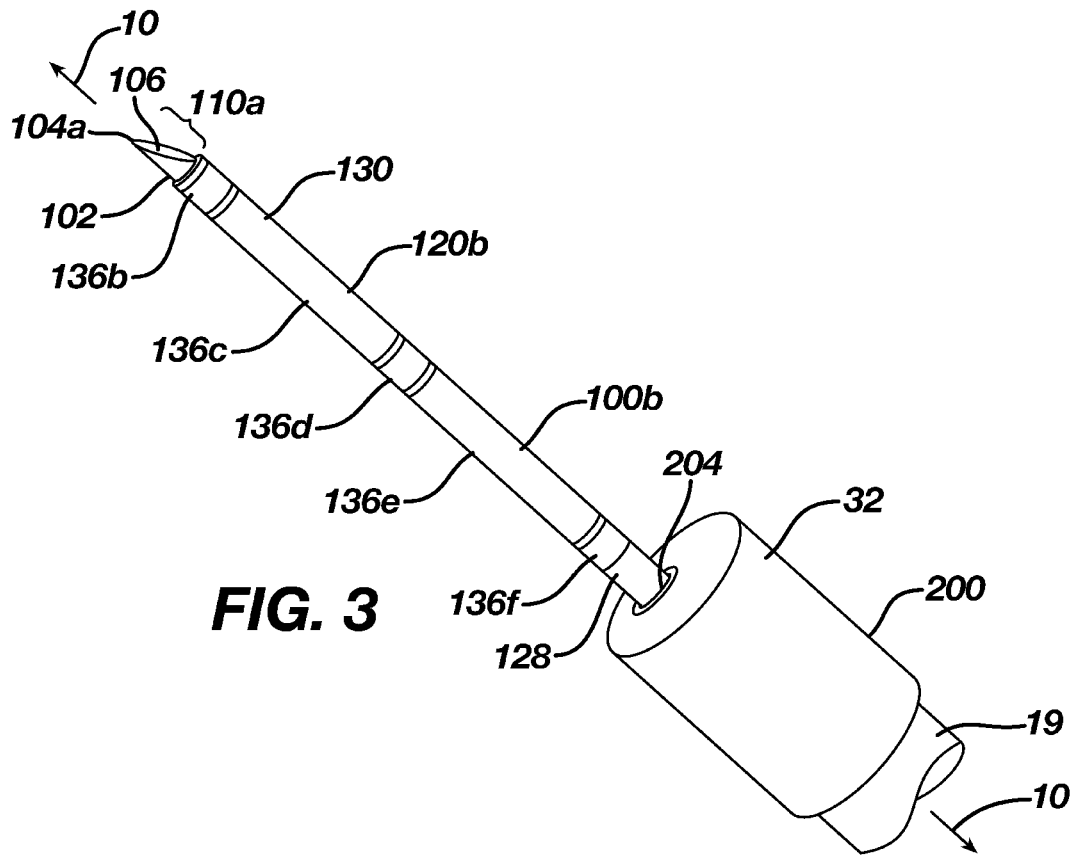
FIG. 3 is an illustration of an ablation tool in accordance with some embodiments of the present disclosure.

FIG. 3 is an illustration of an ablation tool including a needle assembly 100b having multiple electrodes 136b-f and solder pads 132. The electrodes 136b-f can be electrically isolated from each other. The electrodes 136b-f can each be electrically isolated from the sharp end 110a. The multiple solder pads 132 can each respectively electrically connect to some or all of the electrodes 136b-f. The electrodes 136b-f can be connected to solder pads 132 in a one-to-one fashion. Alternatively, an electrode 136b-f can connect to multiple solder pads 132, a solder pad 132 can connect to multiple electrodes 136b-f, and/or an electrode 136b-f can be floating, lacking a solder pad connection. RF ablation energy can be applied separately at each electrode 136b-f to provide differing ablation energy at different tissue depths. Additionally, or alternatively, one or more electrodes 136b-f can be connected to an electrical measurement tool.

Figure 4A:
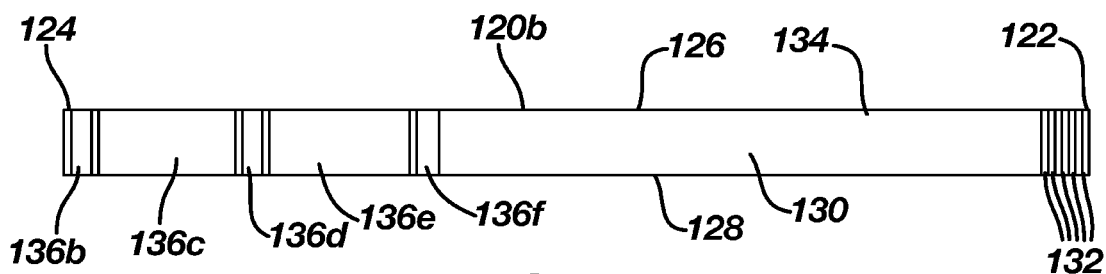
FIG. 4A is an illustration of a flexible circuit of the ablation tool of FIG. 3 in a flat configuration in accordance with some embodiments of the present disclosure.

FIG. 4A is an illustration of the flexible circuit 100b of the ablation tool of FIG. 3 in a flat configuration. In the flat configuration, the electrodes 136b-f can be substantially linear, spanning between the longitudinal edges 126, 128. The solder pads 132 can be substantially linear, spanning between the longitudinal edges 126, 128.

Figure 4B:
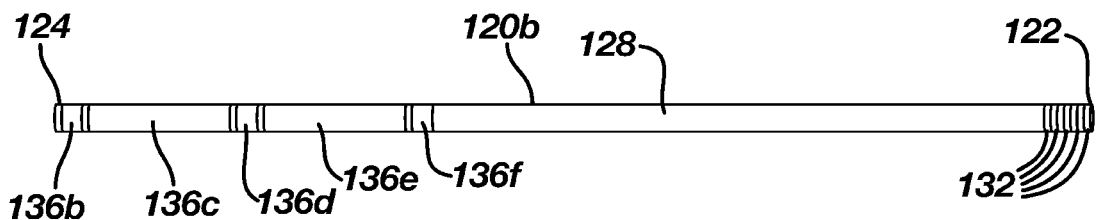
FIG. 4B is an illustration of the flexible circuit of the ablation tool of FIG. 3 in a tubular shape in accordance with some embodiments of the present disclosure.

FIG. 4B is an illustration of the flex circuit 120b of the ablation tool of FIG. 3 in a tubular shape. The linear electrodes 136b-f in the flat configuration can become ring electrodes 136b-136f when the flex circuit 120b is wrapped to the tubular shape.

The ablation system, needle assembly 100b, and component parts thereof illustrated in FIGS. 3, 4A, and 4B can otherwise be constructed, include functionality, and include features as described in relation to the ablation system, needle assembly 100a, and component parts thereof as illustrated and described in relation to FIGS. 1, 2A, and 2B.

Figure 5:
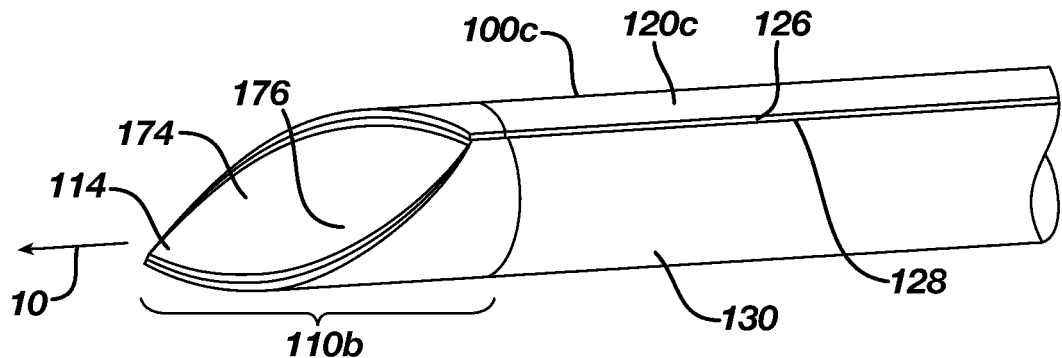
FIG. 5 is an illustration of a flexible circuit in a tubular shape including a pointed end in accordance with some embodiments of the present disclosure.

FIG. 5 is an illustration of a needle assembly 100c including a circuit 120c in a tubular shape including a pointed end 110b. The circuit 120c can be a flexible circuit board that is wrapped to the tubular shape illustrated. Once in the tubular shape, the circuit 120c can have sufficient structural stability and columnar rigidity to perforate tissue during ablation without substantially deforming. In some embodiments, the needle assembly 100c need not include structural support within the lumen 176 of the tubular circuit 120c. The surface of the lumen 176 can correspond to a bottom surface 174 of an electrically insulative substrate film of the flexible circuit board 120c (see also FIG. 11). The lumen 176 of the circuit 120c can further be sized and otherwise configured to provide a fluidic path for conductive fluid to aid in ablation. The lateral sides 126, 128 of the tubular circuit 120c can be fused together or otherwise jointed to create a fluid impermeable seam.

The ablation system, needle assembly 100c, and component parts thereof illustrated in FIG. 5 can otherwise be constructed, include functionality, and include features as described in relation to the ablation system, needle assembly 100a, and component parts thereof as illustrated and described in relation to FIGS. 1, 2A, and 2B. Further, the needle assembly 100c illustrated in FIG. 5 can include multiple electrodes in the electrode region 130 such as illustrated and described in relation to FIGS. 3, 4A, and 4B.

Figure 6:
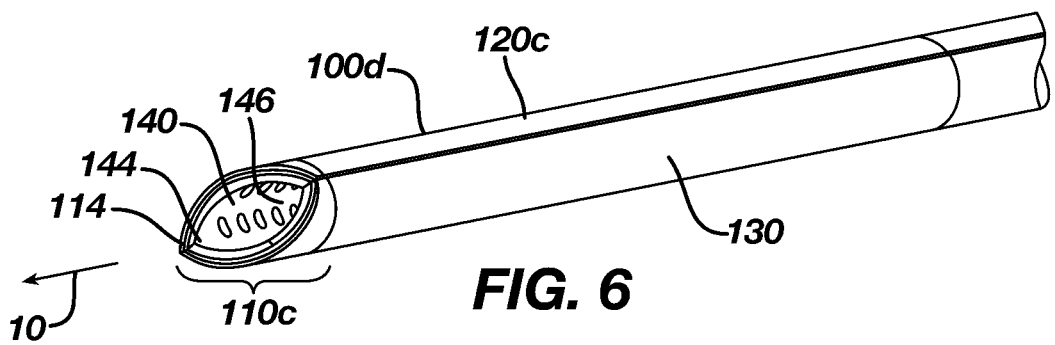
FIG. 6 is an illustration of a flexible circuit having a metal sheet affixed thereto, the flexible circuit and the metal sheet in a tubular shape and including a pointed end in accordance with some embodiments of the present disclosure.

FIG. 6 is an illustration of a needle assembly 100d including a circuit 120c having a metal sheet 140 affixed thereto. The circuit 120c and the metal sheet 140 are illustrated in a tubular shape including a pointed end 110c. The metal sheet 140 can provide additional columnar rigidity to support the tubular circuit 120c. The circuit 120c therefore can, but need not, have sufficient columnar rigidity to lance tissue without significant deformation absent the metal sheet 140. The circuit 120c illustrated in FIG. 6 can otherwise be constructed, include functionality, and include features as described in relation to the circuit 120c illustrated in FIG. 5.

Figure 7:
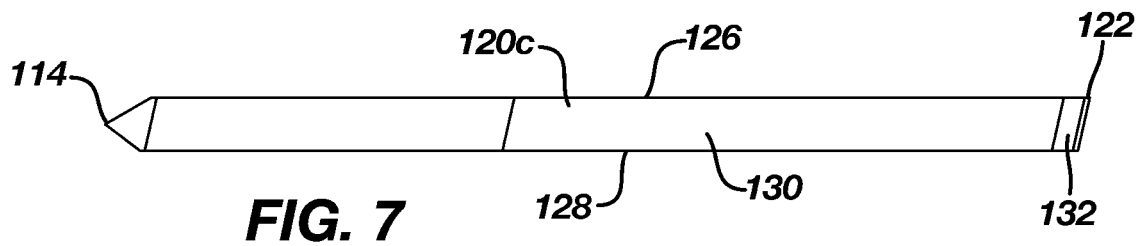
FIG. 7 is an illustration of the flexible circuit of FIG. 5 or FIG. 6 in a flat configuration in accordance with some embodiments of the present disclosure.

FIG. 7 is an illustration of the circuit 120c of FIG. 5 or FIG. 6 in a flat configuration. The circuit 120c can have a triangular shape near the distal end 114 of the flat circuit 120c such that when the circuit 120c is wrapped to form a tube, the triangular shape forms the sharp end 110b illustrated in FIG. 5 or a portion of the sharp end 110c illustrated in FIG. 6. The outer surface 130 of the circuit 120c can be insulative within the triangular shape.

Figure 8A:
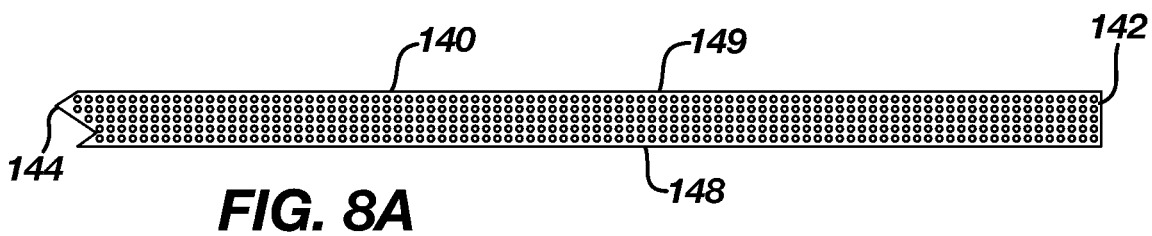
FIG. 8A is an illustration of the metal sheet of FIG. 6 in a flat configuration in accordance with some embodiments of the present disclosure.

FIG. 8A is an illustration of the metal sheet 140 of FIG. 6 in a flat configuration. The metal sheet can have lateral edges 126, 128 that can overlap when the metal sheet 140 is formed in the tubular shape.

Figure 8B:
FIG. 8B is an illustration of the metal sheet of FIG. 6 in a tubular shape in accordance with some embodiments of the present disclosure.

FIG. 8B is an illustration of the metal sheet 140 of FIG. 6 in a tubular shape. The metal sheet 140 can be affixed to the flexible circuit board 120c in either the flat or the tubular shape. The metal sheet 140 can include perforations to reduce weight of the metal sheet 140.

Figure 9:
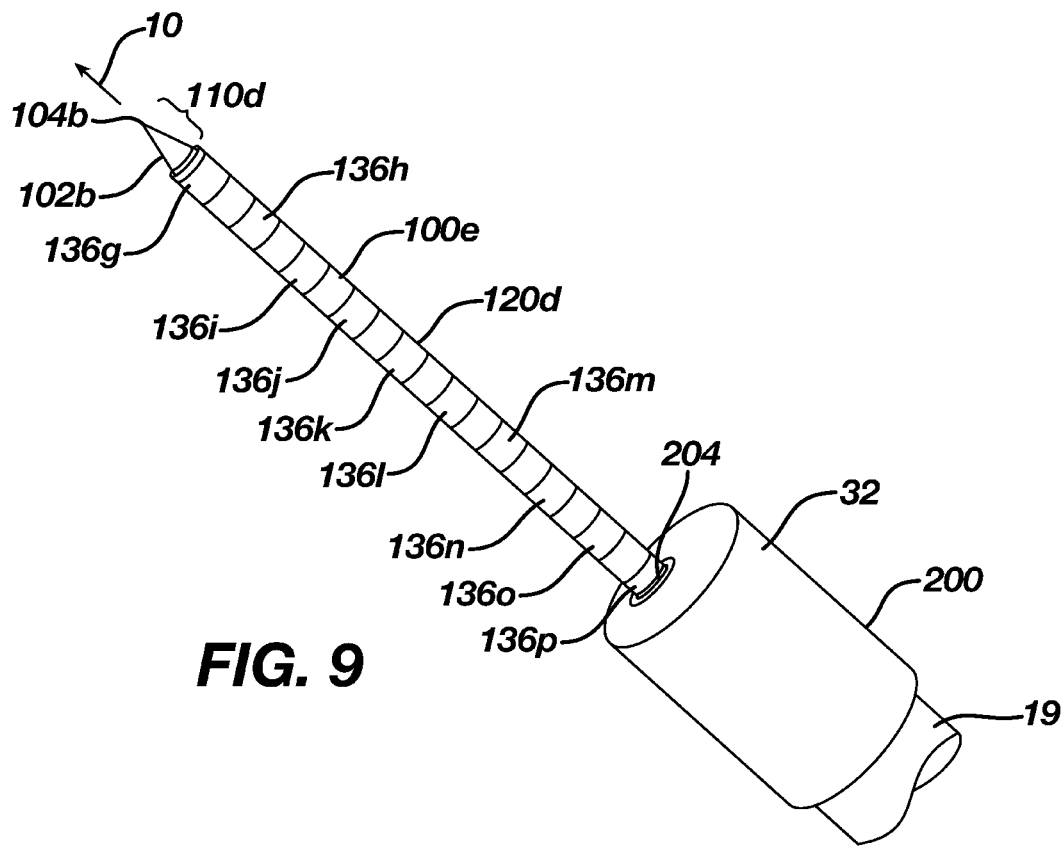
FIG. 9 is an illustration of a diagnostic electrode tool in accordance with some embodiments of the present disclosure.

FIG. 9 is an illustration of a diagnostic electrode tool including a diagnostic needle assembly 100e having multiple electrodes 136g-p. The needle assembly 100e can include a flexible circuit 120d.

Figure 10A:
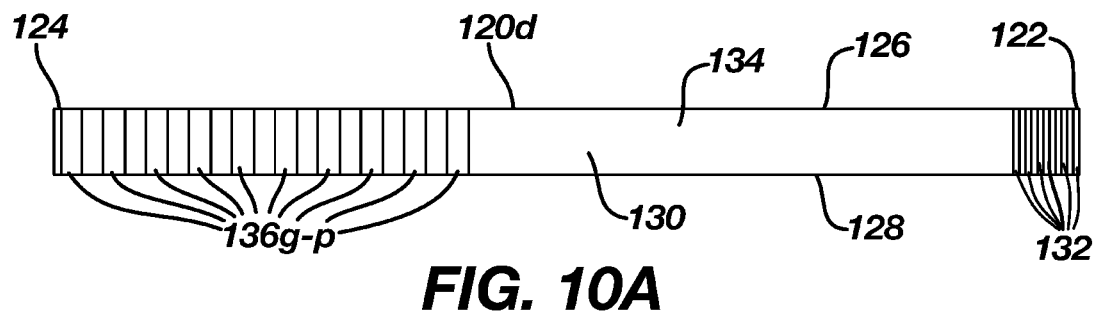
FIG. 10A is an illustration of a flexible circuit of the diagnostic electrode tool of FIG. 9 in a flat configuration in accordance with some embodiments of the present disclosure.

FIG. 10A is an illustration of the flex circuit 120d of the ablation tool of FIG. 9 in a flat configuration. In the flat configuration, the electrodes 136g-p can be substantially linear, spanning between the longitudinal edges 126, 128 of the circuit board 120d. The solder pads 132 can be substantially linear, spanning between the longitudinal edges 126, 128 of the circuit board 120d. In other words, when flat, the flexible circuit 120d can be rectangular with part of the outer surface 130 covered in rectangular bands of sputtered gold 136g-p.

Figure 10B:
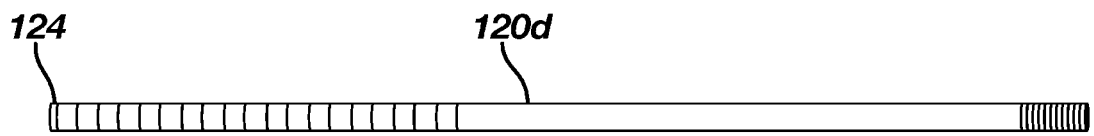
FIG. 10B is an illustration of the flexible circuit of the diagnostic electrode tool of FIG. 9 in a tubular shape in accordance with some embodiments of the present disclosure.

FIG. 10B is an illustration of the flex circuit 120d of the ablation tool of FIG. 9 in a tubular shape. The linear electrodes 136g-p in the flat configuration can become ring electrodes 136g-p when the flex circuit 120d is wrapped to the tubular shape. In other words, when tubular, the rectangular bands of sputtered gold 136g-p can form rings circumscribing the tubular shape.

Referring collectively to FIGS. 9, 10A, and 10B, the needle assembly 100e can further include a needle 102b. The flexible circuit 120d can be wrapped around the needle 102b. The flexible circuit 120d can be affixed to the needle 102b using adhesive, thermal processing, or other means as would be appreciated and understood by a person of ordinary skill in the art. Once formed, the bands 136g-p can form a series of spaced and isolated ring electrodes wrapped laterally around the needle frame (wrapped circumferentially about a longitudinal axis 10). Each electrode 136g-p can be electrically isolated and linked by a trace on the circuit board 120d to a solder pad 132. Lead wires can be attached to the solder pads 132 to link to a diagnostic system.

The ring electrodes 136g-p can be configured to detect bipolar electrocardiograph (ECG) signals, uni-polar ECG signals, impedance, activation voltage, and other electrically detectable signals as would be appreciated and understood by a person of ordinary skill in the art. The array of ring electrodes 136g-p can further be configured to observe myocardium electrical properties at depth. For instance, catheter 200 of the diagnostic electrode tool can include a navigation sensor paired with CARTO mapping and diagnostic software (or similar software as would be appreciated and understood by a person of ordinary skill in the art).

In some embodiments, the diagnostic electrode tool can be configured to serve as a lesion assessment tool. The needle assembly 100e can be moved to penetrate a known lesion location or suspected leak area in a lesion. Once at least some of the electrodes 136g-p are positioned within the tissue, a physician or other user can utilize the electrodes to determine relative tissue impedance at depth. The relative tissue impedance can be used to determine lesion depth, lesion quality, and/or sub lesion signal propagation. Such data can direct additional focused analysis (e.g. RF analysis). Using such a lesion assessment tool, can, in some applications, provide a physician with a means for directly verifying lesion quality or trouble shooting electrically leaking lesions as an alternative to clinical design validation models or indirect measurement with surface diagnostics.

In some embodiments, the diagnostic electrode tool can be configured to serve as a subsurface diagnostic tool. The needle assembly 100e can be moved to penetrate myocardial tissue in multiple locations. At each location, a physician or other user can utilize the electrodes to obtain electrical measurements of the myocardial tissue at multiple depths. The multiple depth readings of myocardial tissue can be overlaid against a marker signal to collate individual observation points. A computing system provided with the multiple depth readings and marker signal can be configured to piece together one or more 3-D models of electrical signal propagation, electrical signal activation, and/or impedance. Triangular boundary conditions can be utilized to identify potential activation points for ablation that are not apparent when performing a similar analysis using surface contact diagnostic devices lacking depth readings.

In some embodiments, the diagnostic electrode tool can serve as an alternative to using a needle ablation catheter as a diagnostic tool. The diagnostic electrode tool having multiple electrodes 136g-p can provide greater granularity in electrical signal modeling compared to a needle ablation catheter having a single ablation electrode. The multiple electrodes 136g-p can essentially act as an antenna array as opposed to one larger antenna in a single electrode tool.

Electrode spacing, electrode surface area, and electrode quantity can be configured according to the needs of a given diagnostic application (e.g. create a clinically useful signal profile). In some embodiments, the circuit board 120d can include about 5 bipolar pairs (about 10 electrodes total). Alternatively, the circuit board 120d can include about 6 electrodes. In some embodiments, electrodes can be evenly spaced with uniform edge-to-edge spacing. Alternatively, electrodes can have a non-uniform edge-to-edge spacing arrangement (e.g. 2 mm-4 mm-2 mm-4 mm-2 mm . . . ) In some embodiments, each of the electrodes can be spaced over a about a 9 mm penetration depth as measured from the tip 104b of the needle 102b along the longitudinal axis 10.

Figure 11:
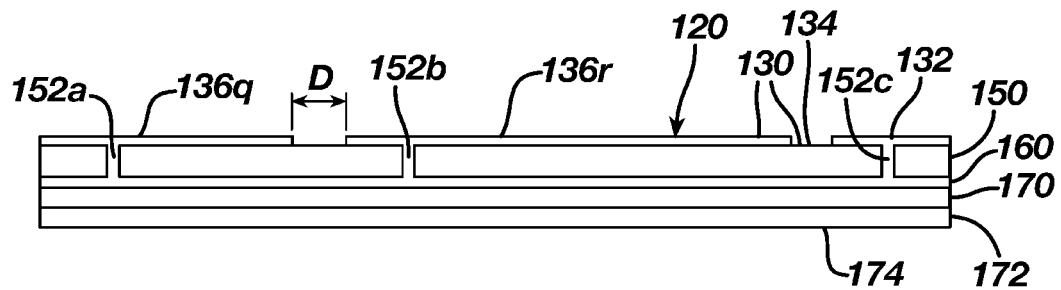
FIG. 11 is an illustration of layers of a flexible circuit usable for an ablation and/or diagnostic tool in accordance with some embodiments of the present disclosure.

FIG. 11 is an illustration of layers of a flexible circuit 120 usable for an ablation and/or diagnostic tool. The flexible circuits 120a-f otherwise illustrated and described herein can be constructed similar to as illustrated in FIG. 11 and described in relation to FIG. 11. The flexible circuit 120 can have a substrate layer 172, an adhesive layer 170, a trace array layer 160, an intermediate electrically insulative layer 150, electrodes 136q-r, and solder pads 132. The flexible circuit 120 can have a bottom surface 174 that includes the bottom side of the substrate layer 172. The flexible circuit 120 can have a top surface 130 that includes top surfaces of the electrodes 136q-r, portions of a top surface of the intermediate electrically insulative layer 150, and top surfaces of the solder pads 132.

The electrodes 136q-r can include gold. The electrodes 136q-r can be pure gold. Electrodes can have a thickness of about 1 micrometer to about 2 micrometers. The electrodes can have an edge-to-edge spacing D. The edge-to-edge spacing D between electrodes can be uniform. Alternatively, the edge-to-edge spacing D can be variable between one pair of electrodes to the next pair of electrodes. Minimum edge-to-edge spacing D between electrodes can be determined by application specific factors such as potential electrical interference between electrodes and limitations of fabrication. Maintaining electrical isolation between adjacent electrodes can be a determining factor for minimum edge-to-edge spacing. In some applications, an edge-to-edge spacing of about 0.05 mm can be achievable with present fabrication techniques and can be sufficient to maintain electrical isolation. In some applications, achieving minimum edge-to-edge spacing may not be an objective.

For the purposes of ablation and/or sensing as described herein, it can be advantageous to use the following spacings. The circuit board 120 can include an edge-to-edge spacing D arrangement of 2 mm-4 mm-2 mm-4 mm-2 mm. The circuit board 120 can include between about 10 electrodes and about 6 electrodes. The electrodes 136q-r can be spaced over a length of between about 7 millimeters to about 9 millimeters from the distal end 124 of the flexible circuit 120. The electrodes 136*s-r* can have a rectangular shape, extending linearly across a width of the flexible circuit 120. A flexible circuit 120 having linear (rectangular) electrodes 136*s-r* can be wrapped to form ring electrodes 136*s-r*.

The intermediate electrically insulative layer 150 can include a polymer such as a flexible polyimide. The intermediate electrically insulative layer 150 can include a Felios RF 775 Polyimide Flex with copper removed. The intermediate electrically insulative layer 150 can have a thickness of about 25 micrometers. Alternatively, the intermediate electrically insulative layer 150 can have a thickness and/or material structure sufficient to achieve structural and electrical functionality as described here. For instance, the intermediate electrically insulative layer can include an electrically insulating flexible sheet having a thickness of about 12.5 micrometers or 50 micrometers as presently commercially available. The intermediate electrically insulative layer 150 can include openings 152*a-c* to provide connection between the electrodes 136*q-r* to traces on the trace array layer 160 and solder pads 132 to traces on the trace array layer 160. The openings 152*a-c* can be filled with a conductive material. The openings 152*a-c* can function as vias.

Figure 12:
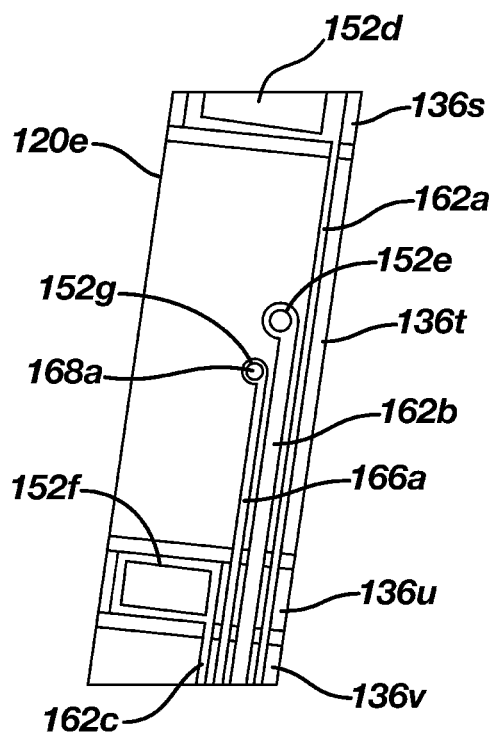
FIG. 12 is an illustration of a flexible circuit including a thermocouple that includes a portion of an electrode in accordance with some embodiments of the present disclosure.
Figure 13:
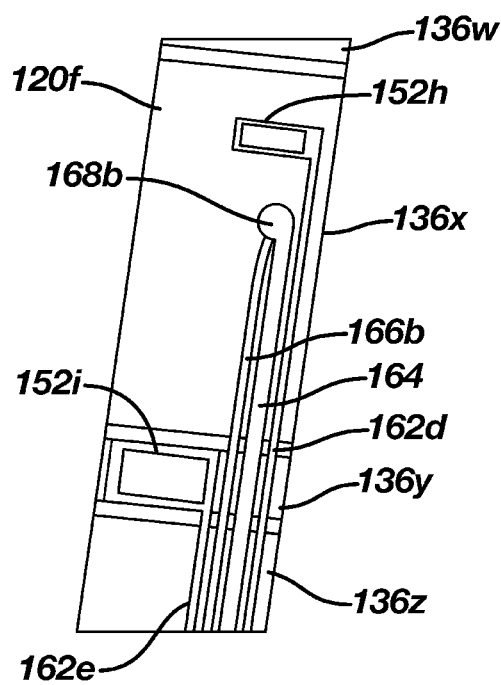
FIG. 13 is an illustration of a flexible circuit including a thermocouple that is electrically isolated from electrodes.

The trace array layer 160 can include electrically conductive traces 162*a-d*, 166*a-b* (see also FIGS. 12 and 13). The traces 162*a-d*, 166*a-b* can have a thickness of about 1 micrometer to about 2 micrometers.

The adhesive layer 170 can have a thickness of about 25 micrometers or less, preferably with a minimum thickness sufficient maintain sufficient adhesion. A thickness of between about 12 micrometers and about 13 micrometers is preferred. In needle assembly embodiments lacking an inner tube (e.g. needle or metallic sheet) for structural support, the adhesive layer 170 can be made thicker as the lack of needle wall thickness allows more space for other layers without affecting the overall size of the needle assembly. The adhesive layer 170 can include an acrylic adhesive. The adhesive can be coated on release paper. The adhesive layer 170 can include a Dupont Pyralux LF sheet adhesive such as LF0100 or similar product.

The substrate layer 172 can have a thickness of between about 12 micrometers and about 13 micrometers. Alternatively, the intermediate electrically insulative layer 150 can have a thickness and/or material structure sufficient to achieve structural and electrical functionality as described here. For instance, the intermediate electrically insulative layer can include an electrically insulating flexible sheet having a thickness of about 12.5 micrometers or 50 micrometers as presently commercially available. The substrate layer 172 can include an acrylic adhesive. The substrate layer can include a polyamide film. The substrate layer 172 can be a composite of an acrylic, polyamide film, and/or other insulative flexible materials. The substrate layer 172 can include a Dupont Pyralus LF coverlay such as LF7001.

FIG. 12 is an illustration of a flexible circuit 120*e* including a thermocouple 168*a* that includes a portion of an electrode 136*t* and a trace 166*a* on the patterned layer 160. The trace 166*a* can include constantan. The trace 166*a* can make contact to the electrode 136*t* through a via 152*g*. Configured as such, the thermocouple junction 168*a* can be separated from an ablation surface of tissue by the sum of the electrode 136*t* thickness and intermediate insulative layer 150 thickness (e.g. about 26 micrometers). The thermocouple 168*a* can thereby be in direct contact with the electrode 136*t*.

The trace array later 160 can further include traces 162*a-c* of the same material as electrodes 136*s-v*. The electrode traces 162*a-c* can each be in contact with a respective electrode 136*s-v* through a respective via 152*d-f*. Some or all of the electrode traces 162*a-c* can each provide a path for ablation current to the respective electrode 136*s-u*. Additionally, or alternatively, some or all of the electrode traces 162*a-c* can provide a path for electrical signal measurement from the respective electrode 136*s-u*.

Each of the traces 162*a-c*, 166*a* can connect to a respective solder pad 132.

FIG. 13 is an illustration of a flexible circuit 120*f* including a thermocouple 168*b* that is electrically isolated from the electrodes 136*w-z*. The thermocouple 168*b* can be confined to the trace array layer 160. The thermocouple 168*b* can include a constantan trace 166*b* and a gold trace 164. The trace array layer 160 can further include electrode traces 162*d-e* in contact with electrodes 136*x-y* through vias 152*h-i*. Each of the traces 162*d-e*, 164, 166*b* can connect to a respective solder pad 132. Some or all of the electrode traces 162*d-e* can each provide a path for ablation current to the respective electrode 136*x-y*. Additionally, or alternatively, some or all of the electrode traces 162*d-e* can provide a path for electrical signal measurement from the respective electrode 136*x-y*.

Referring collectively to FIGS. 11 and 12, a needle assembly 100, 100*a-e* including a flexible circuit 120*e-f* having a thermocouple 168*a-b* integrated therein can be configured to perform temperature controlled ablations through automated temperature feedback from thermocouples 168*a-b*.

Any of the flexible circuits 120, 120*a-f* illustrated herein can include electrodes configured to extract electrical signals for diagnostic purposes in addition to electrodes configured to provide electrical current for ablation. In some embodiments, one or more diagnostic electrodes can be positioned in the distal direction and/or in the proximal direction in relation to each ablation electrode. Positioned as such, the diagnostic electrodes can be configured to provide data to a computing device configured to determined, based on the provided data, whether each respective diagnostic electrode is in contact with scar tissue or activating tissue. The computing device can further be configured to control electrical current output from respective ablation electrodes to target activating tissue. As illustrated in FIGS. 12 and 13, electrodes 136*t*, 136*x* in close proximity to thermocouple junctions 168*a-b* can be configured for ablation while electrodes 136*s*, 136*u*, 136*w*, 136*y* on either side the ablation electrodes 136*t*, 136*x* can be configured as diagnostic electrodes.

Thermocouples 168*a-b* can be placed in relation to the electrode 136*t*, 136*x* surface. Assuming a uniform thickness and shape of an ablative electrode 136*t*, 136*x*, a thermocouple 168*a-b* can be placed centered in the ablative surface to represent the temperature across the surface. Additionally, or alternatively, the thermocouple 168*a-b* can be placed near an edge of the electrode 136*t*, 136*x* to capture boundary temperatures. Multiple ablation zones can be accommodated by shorting to multiple individual or shared constantan traces. Alternatively, a constantan trace can be electrically insulated from the remainder of the constantan traces. In some applications, a thermocouple 168*a* in electrical contact with an electrode 136*t* can have improved thermal performance compared to an isolated thermocouple 168*b* separated from the ablative electrode 136*x* by the thickness of the intermediate electrically insulative layer 150. The thermocouple 168*b* isolated from the electrode 136*x* can have mitigated signal noise compared to the thermocouple 168*a* in electrical contact with the electrode 136*t*.

The thermocouples 168a-b can have greater thermal conductivity to ablative electrodes 136t, 136x compared to thermal conductivity to fluidic flow through the needle assembly lumen 106, 146, 176.

Figure 14:
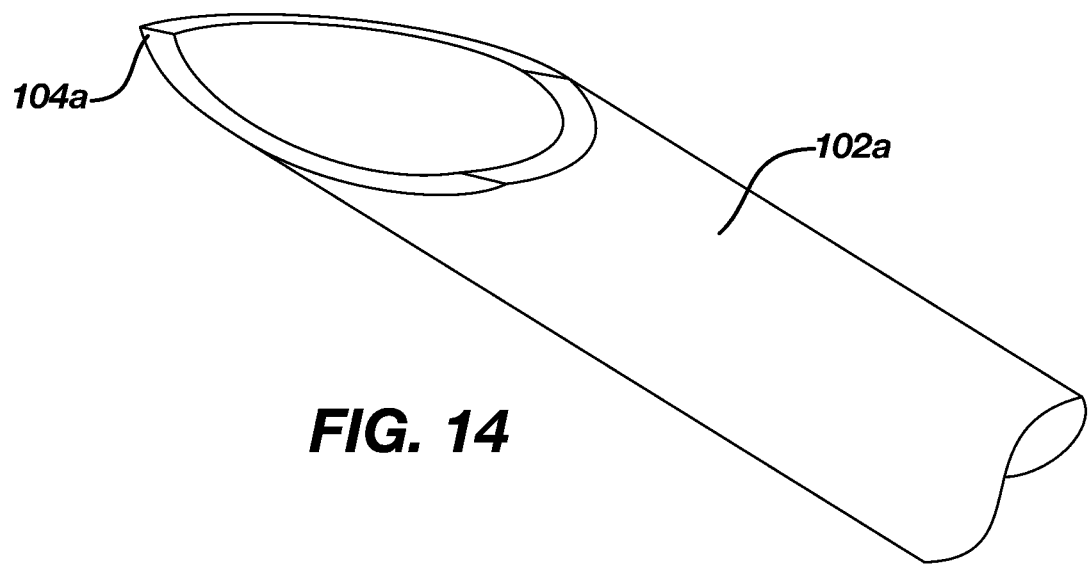
FIG. 14 is an illustration of a sharp end usable for an ablation and/or diagnostic tool in accordance with some embodiments of the present disclosure.

FIG. 14 is an illustration of a sharp end 104a of a needle 102a usable for an ablation and/or diagnostic tool according to the teachings of the present disclosure. The end 104a can have a blade edge. Because the end 104a can be electrically isolated from electrodes 136a-z, the abruptness of the structure need not result in current crowding. Similarly, a needle 102b of a diagnostic tool can include a pointed tip 104b according to the teachings of the present disclosure.

Figure 15:
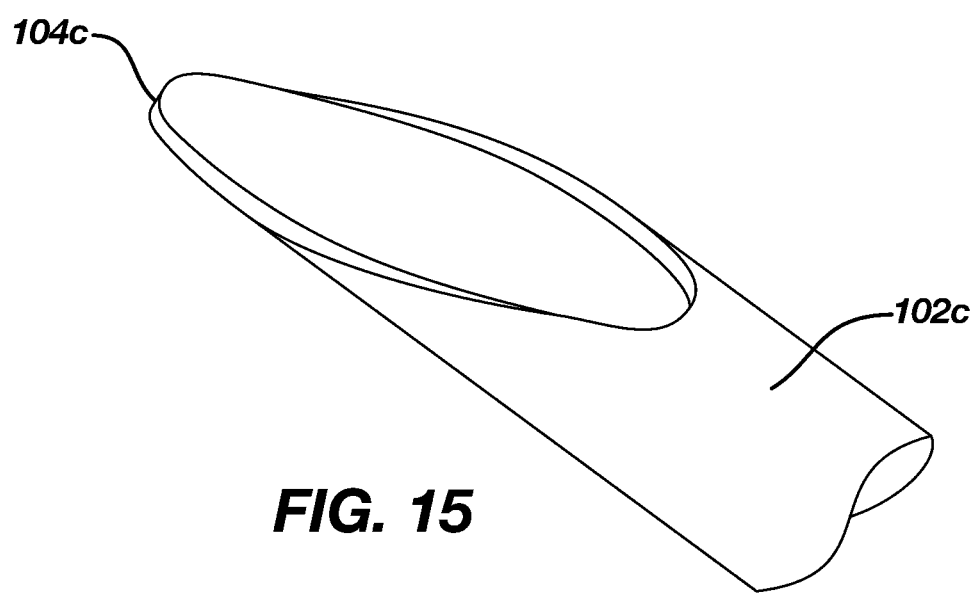
FIG. 15 is an illustration of a domed end of an ablation tool as is known.

FIG. 15 is an illustration of a rounded end 104c of a needle 102c usable for an ablation and/or diagnostic tool where the needle 102c serves as an ablation electrode as known in the art. The end 104c is rounded to mitigate effects of current crowding and hot spots during ablation.

Figure 16:
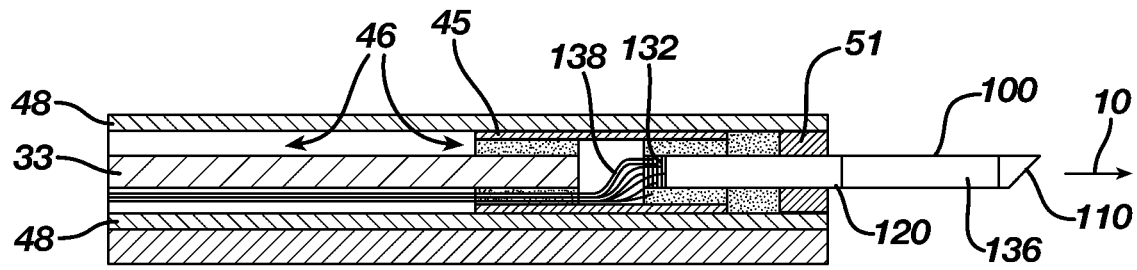
FIG. 16 is an illustration of a needle electrode assembly in accordance with some embodiments of the present disclosure.

FIG. 16 is a cross-sectional illustration of a needle electrode assembly 46 including a needle assembly 100, an outer tube 48, proximal tubing 33, joining tubing 45, a spacer 51, and wiring 138. Any of the needle assemblies 100a-e illustrated and otherwise described herein can be affixed as part of a needle electrode assembly such as the needle assembly 100 is illustrated in relation to the needle electrode assembly 46 in FIG. 16.

The needle electrode assembly 46 can be aligned along a longitudinal axis 10. The spacer 51 can inhibit bodily fluid from entering the needle electrode assembly 46. A portion of the flexible circuit 120 can be positioned within the outer tube 48. The flexible circuit 120 can be otherwise configured as any of the flexible circuits 120a-f otherwise described and illustrated herein. The electrode section 136 of the flexible circuit 120 can be affixed external to the outer tube 48 such that the electrodes are positioned to enter tissue upon penetration by the needle assembly 100. Wires 138 can extend through the outer tube 48 and can be accessible to a physician or other user during a treatment. The wires 138 can be connected to a RF generator, other ablation energy source, voltmeter, ohmmeter, ammeter, and/or other electrical measurement tool.

FIG. 17 is an illustration of an ablation or diagnostic tool. The needle electrode assembly 46 including the needle assembly 100 can be slidably positioned within a protective tubing or sheath 47 affixed stationary in relation to the catheter 200. The needle electrode assembly 46 can be retracted such that the sharp end 110 of the needle assembly 100 is retracted into the sheath 47. The sharp end 110 can be configured as any of the sharp ends 110a-d otherwise described and illustrated herein. The catheter 200 can include an infusion lumen 24 in fluidic communication with the lumen 106, 146, 176 of the needle assembly 100, 100a-e.

The catheter 200 can include a navigation sensor 70. The navigation sensor 70 can be contained within the catheter 200 near the distal end of the catheter 200. The navigation sensor 70 can be used to detect movement of an electrode 136a-z of the needle assembly 100 in relation to the distal end of the catheter 200. The navigation sensor 70 can further be used to determine the coordinates of the distal end of the catheter 200. The navigation sensor 70 can be connected to a sensor cable 72. The sensor cable 72 can extend through a lumen 28 of the catheter 200 and can be connected to an electrical measurement tool.

The catheter 200 can include a tip electrode 32. The tip electrode 32 can include a passage 56 through which the sheath 47 extends. The tip electrode 32 can be connected to tubing 19 by a plastic housing 34. The tip electrode 32 can be configured to measure electrical signals at tissue surface.

The catheter 200 can further include a ring electrode 38 configured to measure electrophysiology. The tip electrode 32 and ring electrode 38 can each be connected to a separate lead wire 40. The wires 40 can be connected to electrical measurement tools.

By combining the navigation sensor 70 and the electrodes 32, 38, a physician or other user can simultaneously map contours or shape of a heart chamber, electrical activity of the hear, and extent of displacement of the catheter 200.

Figure 18:
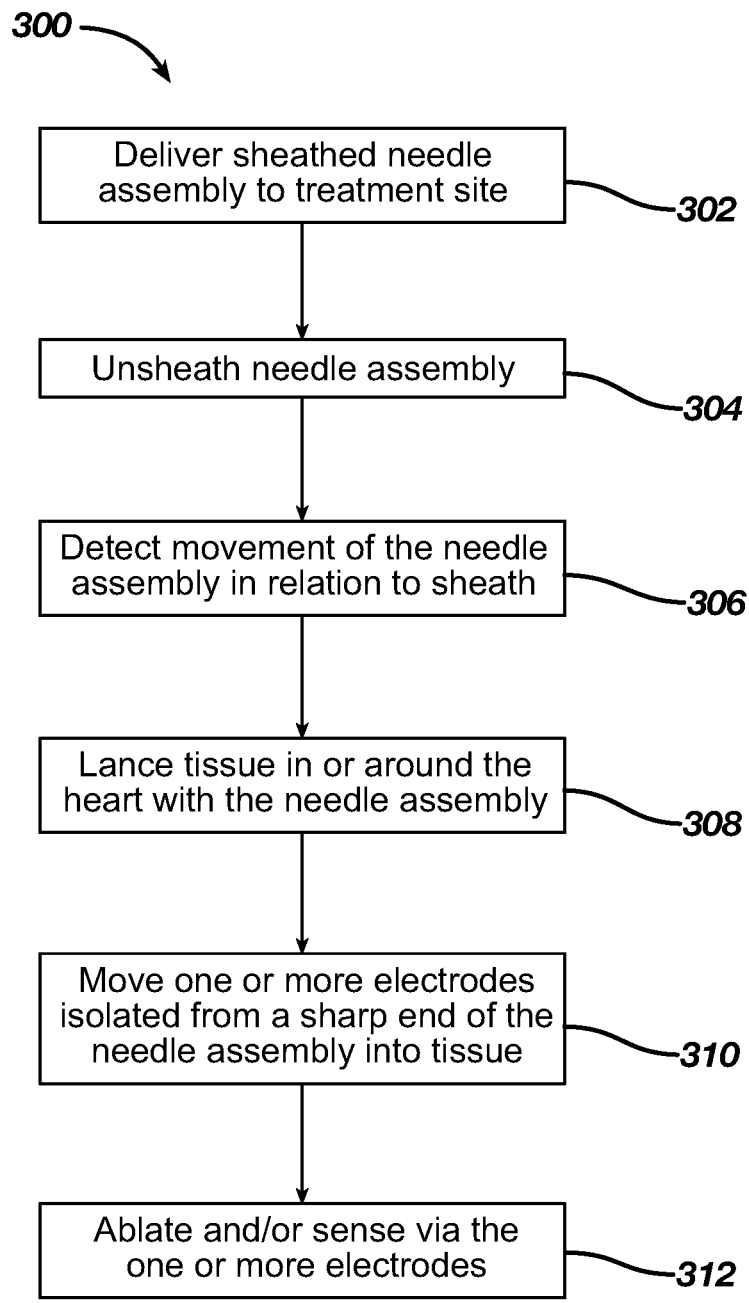
FIG. 18 is a flow diagram for a method of treatment using an ablation or diagnostic tool in accordance with embodiments of the present disclosure.

FIG. 18 is a flow diagram illustrating a method 300 of treatment using an ablation or diagnostic tool. The method 300 can include one or more of the following steps presented in no particular order. The example method 300 can include additional steps as would be appreciated and understood by a person of ordinary skill in the art. The example method can be performed by a physician or other user utilizing an example diagnostic and/or ablation tool including a needle assembly 100, 100a-e as illustrated and disclosed herein, a variation thereof, or an alternative thereto as would be appreciated and understood by a person of ordinary skill in the art.

At step 302, a sheathed needle assembly can be delivered to a treatment site. The needle assembly can be a needle assembly 100, 100a-e as illustrated and disclosed herein, a variation thereof, or an alternative thereto as would be appreciated and understood by a person of ordinary skill in the art. The needle assembly can be sheathed within a catheter or other sheath such as catheter 200 as illustrated and disclosed herein, a variation thereof, or an alternative thereto as would be appreciated and understood by a person of ordinary skill in the art.

At step 304, the needle assembly can be unsheathed. The needle assembly can be unsheathed by sliding the needle assembly out of an opening in a distal end of a catheter or other sheath. For instance, the needle assembly 100, 100a-e can be slid out of opening 204 of catheter 200 as illustrated and disclosed herein, a variation thereof, or an alternative thereto as would be appreciated and understood by a person of ordinary skill in the art.

At step 306, movement of the needle assembly in relation to the sheath can be detected. For instance, the catheter can include a navigation sensor such as the navigation sensor 70 as illustrated and disclosed herein, a variation thereof, or an alternative thereto as would be appreciated and understood by a person of ordinary skill in the art. The navigation sensor can be configured to detect movement of the needle assembly in relation to the navigation sensor. The needle assembly can be configured to move in only one dimension in relation to the navigation sensor.

At step 308, tissue in or around the heart can be lanced with the needle assembly. The needle assembly can include a sharp end shaped to lance tissue such as a sharp end 110, 110a-d as illustrated and disclosed herein, a variation thereof, or an alternative thereto as would be appreciated and understood by a person of ordinary skill in the art.

At step 310, one or more electrodes isolated from the sharp end of the needle assembly can be moved into the tissue.

At step 312, one or more of the electrodes can be used to ablate and/or sense tissue.

The descriptions contained herein are examples of embodiments of the invention and are not intended in any way to limit the scope of the invention. As described herein, the invention contemplates many variations and modifications of ablation tools and diagnostic tools, including alternative numbers of electrodes, alternative combinations of electrodes, combinations of components illustrated in separate figures, alternative materials, alternative component geometries, and alternative component placement. Modifications and variations apparent to those having ordinary skill in the art according to the teachings of this disclosure are intended to be within the scope of the claims which follow.

What is claimed is:

1. A device for lancing intravascular tissue, the device comprising:
a circuit defining an outer surface disposed about a longitudinal axis to define a tubular shape that (i) extends along the longitudinal axis from a first end of the circuit to a proximal portion of the circuit and (ii) comprises columnar rigidity sufficient to lance intravascular tissue, the circuit comprising:
an electrically insulative substrate film,
a patterned layer disposed over the electrically insulative substrate film and comprising electrically conductive traces,
an electrically insulative isolating film disposed over the patterned layer and comprising one or more vias therethrough,
one or more electrodes disposed over the electrically insulative isolating film and on the outer surface of the tubular shape,
a first thermocouple junction positioned at a first via of the one or more vias, the first thermocouple junction comprising a portion of a first electrode of the one or more electrodes in contact with a first electrically conductive trace of the electrically conductive traces, and
a second thermocouple junction residing in the patterned layer, the second thermocouple junction comprising a portion of a second electrically conductive trace of the electrically conductive traces and a portion of a third electrically conductive trace of the electrically conductive traces, and the portion of the second electrically conductive trace and the portion of the third electrically conductive trace being in electrical contact,
the electrically insulative substrate film, the patterned layer, and the electrically insulative isolating film each being shaped to define a pointed tip approximate the first end of the circuit, the pointed tip being shaped to lance the intravascular tissue.

2. The device of claim 1,
the circuit further comprising a metal sheet under the electrically insulative substrate film,
the metal sheet comprising a pointed tip approximate the first end of the circuit,
the metal sheet being disposed on an inner surface of the tubular shape,
the tubular shape comprising the metal sheet.

3. The device of claim 1, at least one of the one or more electrodes respectively comprising a gold band encircling the tubular shape.

4. The device of claim 1, further comprising:
a sheath surrounding the circuit and the pointed tip, through which the circuit and pointed tip are slidable to extend the pointed tip out of the sheath.

5. The device of claim 1,
the first electrode comprising gold, and
the first electrically conductive trace comprising constantan.

6. The device of claim 1, further comprising:
a navigation sensor positioned to detect a movement of an electrode of one or more electrodes.

7. The device of claim 6, further comprising:
a catheter comprising a distal end; and
a needle assembly comprising the circuit and the pointed tip, the needle assembly translatable in one dimension in relation to the navigation sensor, the navigation sensor being affixed approximate the distal end of the catheter.

8. A system comprising:
a circuit defining an outer surface disposed about a longitudinal axis to define a tubular shape that (i) extends along the longitudinal axis from a first end of the circuit to a proximal portion of the circuit and (ii) comprises columnar rigidity sufficient to lance intravascular tissue, the circuit comprising:
an electrically insulative substrate film,
a patterned layer disposed over the electrically insulative substrate film and comprising electrically conductive traces,
an electrically insulative isolating film disposed over the patterned layer and comprising one or more vias therethrough,
a plurality of electrodes disposed over the electrically insulative isolating film and on the outer surface of the tubular shape, each electrode being electrically connected to a respective electrically conductive first trace of a plurality of electrically conductive first traces of the electrically conductive traces on the patterned layer,
a first thermocouple junction positioned at a first via of the one or more vias, the first thermocouple junction comprising a portion of a first electrode of the plurality of electrodes in contact with a second electrically conductive trace, different from the respective electrically conductive first traces of the plurality of electrically conductive first traces, of the electrically conductive traces, and
a second thermocouple junction residing in the patterned layer, the second thermocouple junction comprising a portion of a third electrically conductive trace of the electrically conductive traces and a portion of a fourth electrically conductive trace of the electrically conductive traces, and the portion of the third electrically conductive trace and the portion of the fourth electrically conductive trace being in electrical contact;
a catheter extending in a distal direction from the circuit;
conductive wires each respectively electrically connected to the respective electrically conductive first traces of the plurality of electrically conductive first traces of the electrically conductive traces, the conductive wires extending through the catheter; and
a radio frequency generator electrically connected to at least one of the conductive wires,
the electrically insulative substrate film, the patterned layer, and the electrically insulative isolating film each being shaped to define a pointed tip approximate the first end of the circuit, the pointed tip being shaped to lance the intravascular tissue.

9. The system of claim 8, further comprising:
an electrical measurement tool electrically connected to a first portion of the plurality of electrodes,
the radio frequency generator being electrically connected to a second portion of the plurality of electrodes.

10. The system of claim 9, the electrical measurement tool comprising one or more of a voltmeter, an ohmmeter, and an ammeter.

11. The system of claim 9, further comprising:

a navigation sensor positioned approximate a distal end of the catheter.

12. A method of intravascular treatment comprising:

delivering an electrode needle assembly intravascularly via a catheter, the electrode needle assembly comprising:

- a circuit defining an outer surface disposed about a longitudinal axis to define a tubular shape that (i) extends along the longitudinal axis from a first end of the circuit to a proximal portion of the circuit and (ii) comprises columnar rigidity sufficient to lance intravascular tissue, the circuit comprising:
  - an electrically insulative substrate film,
  - a patterned layer disposed over the electrically insulative substrate film and comprising electrically conductive traces,
  - an electrically insulative isolating film disposed over the patterned layer and comprising one or more vias therethrough,
  - one or more electrodes disposed over the electrically insulative isolating film and on the outer surface of the tubular shape,
  - a first thermocouple junction positioned at a first via of the one or more vias, the first thermocouple junction comprising a portion of a first electrode of the one or more electrodes in contact with a first electrically conductive trace of the electrically conductive traces, and
  - a second thermocouple junction residing in the patterned layer, the second thermocouple junction comprising a portion of a second electrically conductive trace of the electrically conductive traces and a portion of a third electrically conductive trace of the electrically conductive traces, and the portion of the second electrically conductive trace and the portion of the third electrically conductive trace being in electrical contact,
  - the electrically insulative substrate film, the patterned layer, and the electrically insulative isolating film each being shaped to define a pointed tip approximate the first end of the circuit, the pointed tip being shaped to lance the intravascular tissue;

lancing the intravascular tissue in or around a heart with the electrode needle assembly; and moving the first electrode of the electrode needle assembly to a first depth within the intravascular tissue while moving a second electrode of the electrode needle assembly to a second depth shallower than the first depth.

13. The method of claim 12, further comprising:

applying a radio frequency electrical signal to at least one of the first electrode and the second electrode.

\* \* \* \* \*